(12) United States Patent
Koop et al.

(10) Patent No.: US 7,122,029 B2
(45) Date of Patent: *Oct. 17, 2006

(54) THERMAL QUENCHING OF TISSUE

(75) Inventors: Dale E. Koop, Woodside, CA (US); Jonathan M. Baumgardner, Roseville, CA (US); Robert A. Weiss, Hunt Valley, MD (US)

(73) Assignee: CoolTouch Incorporated, Roseville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/031,154

(22) Filed: Jan. 7, 2005
(Under 37 CFR 1.47)

(65) Prior Publication Data
US 2005/0154383 A1 Jul. 14, 2005

Related U.S. Application Data

(60) Division of application No. 10/160,579, filed on May 31, 2002, now abandoned, which is a continuation-in-part of application No. 09/364,275, filed on Jul. 29, 1999, now Pat. No. 6,451,007.

(51) Int. Cl.
*A61B 18/18* (2006.01)
*A61B 18/20* (2006.01)
*A61B 18/04* (2006.01)
*A61F 7/00* (2006.01)

(52) U.S. Cl. .................. 606/9; 606/27; 607/88; 607/96; 128/898

(58) Field of Classification Search .................. 606/8, 606/9, 20–31; 607/88, 89, 96–111; 128/898
See application file for complete search history.

(56) References Cited

U.S. PATENT DOCUMENTS

| 3,630,203 A | 12/1971 | Sellinger et al. |
|---|---|---|
| 4,020,383 A | 4/1977 | Labadini et al. |
| 4,376,376 A | 3/1983 | Gregory |

(Continued)

OTHER PUBLICATIONS

Spatially selective photocoagulation of biological tissues: feasibiliy study utilizing cryogen spray cooling, Applied Optics; vol. 35, No. 19; Anvarie et al., Jul. 1, 1996, 9 pages.

(Continued)

Primary Examiner—A. Farah
(74) Attorney, Agent, or Firm—Ray K. Shahani, Esq.

(57) ABSTRACT

The present invention provides a system for achieving erythema and/or mild edema in an upper layer of skin, without causing blisters, and without the risk of high fluence levels or critical need for cooling.

3 Claims, 4 Drawing Sheets

U.S. PATENT DOCUMENTS

| | | |
|---|---|---|
| 5,746,735 A | 5/1998 | Furumoto et al. |
| 5,746,736 A | 5/1998 | Tankovich |
| 5,810,801 A | 9/1998 | Anderson et al. |
| 5,814,040 A | 9/1998 | Nelson et al. |
| 5,820,626 A | 10/1998 | Baumgardner |
| 5,885,274 A | 3/1999 | Fullmer et al. |
| 5,928,222 A | 7/1999 | Kleinerman |
| 5,968,034 A | 10/1999 | Fullmer et al. |
| 5,979,454 A | 11/1999 | Anvari et al. |
| 6,059,820 A | 5/2000 | Baronov |
| 6,171,301 B1 * | 1/2001 | Nelson et al. .................. 606/9 |
| 6,248,103 B1 | 6/2001 | Tannenbaum et al. |
| 6,451,007 B1 * | 9/2002 | Koop et al. ..................... 606/9 |
| 6,676,655 B1 * | 1/2004 | McDaniel ....................... 606/9 |

OTHER PUBLICATIONS

Selective cooling of biological tissues: application for thermally mediated therapeutic procedures, Anvari et al., Phys. Med. Biol. 40 (1995) 241-252.

Handpiece Extender brochure, Spectrum Medical Technologies, Inc., RD 1100, RD 1200, 2 pages.

Anvari et al., Spatially Selective Photocoagulation of Biological Tissues: A Feasibility Study Utilizing Cryogen Spray Cooling. App. Optics, in press as of Jan. 8, 1996.

Omega Micro Infrared Temperature Transducer OS40 Series. Omega Complete Temperature Measurement Handbook and Encyclopedia (a registered trademark), J-97 and J-98 (2004).

* cited by examiner

THERMAL QUENCHING OF TISSUE

RELATED APPLICATIONS

This application is a divisional application of U.S. Ser. No. 10/160,579 filed May 31, 2002 now abandoned entitled THERMAL QUENCHING OF TISSUE, which is a continuation in part of U.S. Ser. No. 09/364,275 filed Jul. 29, 1999, now U.S. Pat. No. 6,451,007, entitled THERMAL QUENCHING OF TISSUE.

FIELD OF THE INVENTION

This invention is related to the delivery of laser or other source of thermal energy to biological or other tissue for treatment therein.

BACKGROUND OF THE INVENTION

It is sometimes desirable to cause heat affected changes in a selected structure in tissue, such as a vein or hair follicle without causing heat affected changes in tissue adjacent to the selected structure. Selective photothermalysis is a method of irradiating with a laser or pulsed light source that is preferentially absorbed by a pre-selected target. The amount of energy or fluence delivered to the target is chosen such that the temperature rise in the targeted region results in an intended thermal treatment of the target.

Heating of the epidermis may occur during treatment of the target and several methods have been described for cooling the surface of skin during and prior to treatment to minimize the risk of thermal injury to tissue adjacent to the targeted veins. One early method included pre-cooling with ice for several minute prior to treatment. U.S. Pat. No. 5,282,797 issued Feb. 1, 1994 to Chess describes a method of circulating cooling fluid over a transparent plate in contact with the treatment area to cool the epidermis during treatment. U.S. Pat. No. 5,344,418 issued Sep. 6, 1994 to Ghaffari describes a method whereby a coolant is used for a predetermined time interval in coordination with the delivery of laser energy to optimize the cooling of the epidermis and minimize cooling of the targeted vessel. U.S. Pat. No. 5,814,040 issued Sep. 29, 1998 to Nelson et al. describes a cooling method whereby a cryogenic spurt is applied for a predetermined short time directly onto the skin in the target region. The time period for cooling is confined only to the epidermis while leaving the temperature of deeper port wine stains substantially unchanged. Many of the cooling methods may limit the amount of significant thermal damage to the epidermis during treatment.

It may be desirable to shrink collagen in order to reduce the appearance of undesirable conditions of the skin such as acne scars and wrinkles. The following U.S. patents to Sand teach controlled thermal shrinkage of collagen fibers in the cornea using light at wavelengths between 1.8 and 2.55 microns: U.S. Pat. No. 4,976,709, Class No. 606/5, issued Dec. 11, 1990; U.S. Pat. No. 5,137,530; U.S. Pat. No. 5,304,169; U.S. Pat. No. 5,374,265; and U.S. Pat. No. 5,484,432.

U.S. Pat. No. 5,810,801, class no. 606/9 issued Sep. 22, 1998 to Anderson et al. teaches a method and apparatus for treating wrinkles in skin by targeting tissue at a level between 100 microns and 1.2 millimeters below the surface, to thermally injure collagen without causing erythema, by using light at wavelengths between 1.3 and 1.8 microns. Because of the high scattering and absorption coefficients, precooling is utilized to prevent excess heat build up in the epidermis when targeting the region of 100 microns to 1.2 mm below the surface. Specific laser and cooling parameters are selected so as to avoid erythema and achieve improvement in wrinkles as the long term result of a treatment.

ADVANTAGES AND SUMMARY OF THE INVENTION

The present invention provides a system for achieving erythema and/or mild edema in an upper layer of skin, without causing blisters, and without the risk of high fluence levels or critical need for cooling.

The invention uses a source of thermal energy, which may be infrared in the wavelength range of 1100 nm to 2.9 nm, to cause thermally mediated effects in skin. The systems and methods are directed toward heating the skin with a source of energy which is uniformly attenuated with depth in skin for a predetermined time period and predetermined fluence so that the exposure time of the epidermis and the peak temperature reached by the epidermis are such that the epidermis does not blister but the thermally mediated injury in the skin below the epidermis causes a transient erythema to initiate a healing response. By achieving erythema and/or mild edema in an upper layer of skin, the system precludes the risk of high fluence levels or critical need for cooling. The dosage and time period of application are adjusted to prevent excess accumulation of heat in the epidermis, which would cause tissue damage. Thermal quenching is used to remove latent heat from the treatment site to prevent thermal damage to the tissue. Collagen remodeling is induced by distributing the laser energy over a series of more benign treatments spaced weeks apart.

It is therefore an advantage and an object of the present invention to provide an improved system for selectively cooling tissue during photothermal treatment.

It is a further advantage of the present invention to provide such a system which uses dynamic cooling to quench heat build up during and after photothermal treatment.

It is a further advantage of the present invention to provide such a system which selectively heats a subsurface structure in tissue and subsequently quenches heat build up in non-target tissue.

It is a further advantage of the present invention to reduce the level of pulsed energy needed for treatment by minimizing precooling of the tissue.

It is a further advantage of the present invention to provide such a system which selectively heats a subsurface structure in skin to cause thermal affected changes in said subsurface structure without significant epithelial damage due to subsequent heating from the target region.

It is a further advantage of the present invention to provide such a system which selectively heats vascular lesions in tissue and quenches subsequent heat build up in epithelial tissue.

It is a further advantage of the present invention to provide such a system which selectively heats hair follicles in tissue and quenches subsequent heat build up in epithelial tissue.

It is a further advantage of the present invention to require less cooling of the target area than is typically required, resulting in more efficient heating of the selected target and less thermal damage to surrounding tissue.

In a preferred embodiment, the system for generating light energy is a laser system such as but not limited to a solid-state laser, including but not limited to a neodymium-doped yttrium-aluminum-garnet (Nd:YAG) laser.

In additional preferred embodiments, the system for generating light energy is a gas discharge flashlamp or an incandescent-type filament lamp.

The energy from the generating system may be directed into or coupled to a delivery device such as but not limited to a fiber optic or articulated arm for transmitting the light energy to the target tissue.

The light energy may be focused on tissue with a focusing lens or system of lenses.

The surface of the tissue may be cooled with a cooling device including but not limited to an irrigating solution, a spray or flow of refrigerant or other cryogenic material, or a transparent window cooled by other active means, or other dynamic or passive cooling means.

The tissue may be preheated with a heating device such as, but not limited to an intense light source, a flashlamp, a filament lamp, laser diode, other laser source, electrical current, or other electromagnetic or mechanical energy which penetrates into layers of tissue beneath the surface. The preheating can occur simultaneously or just prior to the surface cooling of tissue from the cooling device such that the tissue preheating results in a temperature rise in underlying layers of tissue, and a temperature profile results. The pulsed application of energy from the energy delivery device results in a temperature profile that preferentially heats a selected structure or target in tissue, and the post cooling prevents thermal damage to tissue adjacent to that structure. This also reduces the overall pulse energy level needed of the pulsed treatment device due to the fact that a desirable temperature profile exists prior to delivery of the pulsed treatment energy.

The tissue may be post cooled with a dynamic cooling device such as, but not limited to a pulse, spray or other flow of refrigerant such that the post cooling occurs after a temperature rise in an underlying targeted structure and a temperature profile results such that the pulsed application of energy from the energy delivery device results in a temperature profile that preferential heats a selected structure in tissue without subsequent undesirable heating to tissue adjacent to that structure from thermal conduction.

Numerous other advantages and features of the present invention will become readily apparent from the following detailed description of the invention and the embodiments thereof, from the claims and from the accompanying drawings.

Various objects, features, aspects and advantages of the present invention will become more apparent from the following detailed description of preferred embodiments of the invention, along with the accompanying drawings in which like numerals represent like components.

Further objects and advantages of the present invention will be come apparent through the following descriptions, and will be included and incorporated herein.

DETAILED DESCRIPTION OF THE PREFERRED EMBODIMENT

Figure 1:
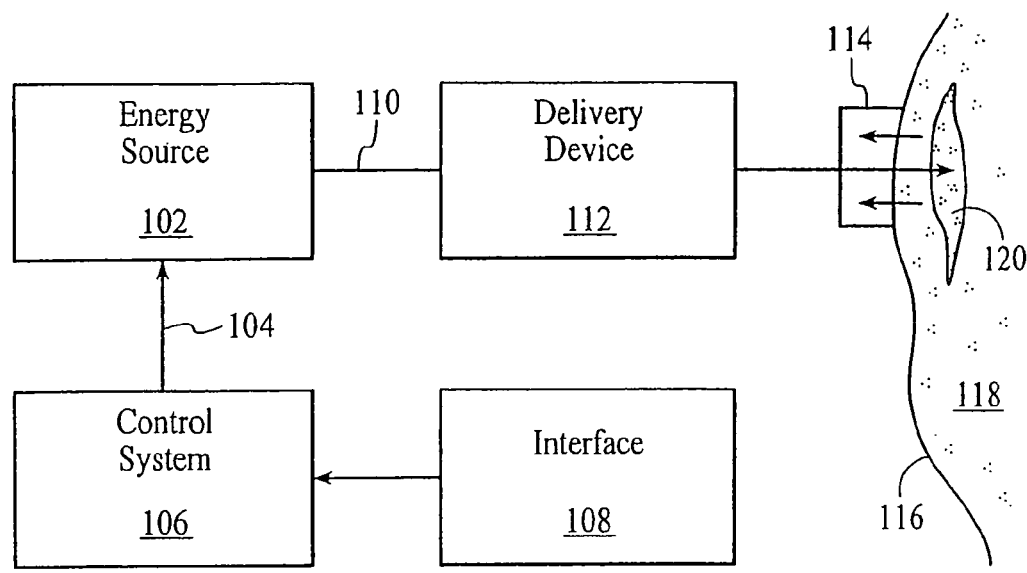
FIG. 1 is a representative schematic block diagram of a preferred embodiment of a system for thermal quenching of tissue of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

FIG. 1 is a representative schematic block diagram of a preferred embodiment of a system 100 for thermal quenching of tissue of the present invention. Operation of energy source 102 to produce energy for delivery by the system 100 is controlled according to control signal 104 from control system 106. Control system 106 includes a physician interface 108 for operating the system. Said interface 108 optionally includes a footswitch for energy delivery, display and interactive and/or menu driven operation utilizing operator input, prompts, etc. Additional energy delivery control interface means shall be known to those skilled in the art.

In a preferred embodiment, energy source 102 is a neodymium doped yttrium-aluminum-garnet (Nd:YAG) laser, energized by a flash-lamp or laser diode. Energy source 102 is controlled by control system 106 which comprises the software and electronics to monitor and control the laser system, and interface 108. The beam of laser energy I 10 from the energy source 102 is directed into a delivery device 112 which may be an optical fiber, a fiber bundle or articulated arm, etc.

Modern instruments to provide dynamic cooling of the surface layers of tissue or other materials are well suited to these applications. A coolant spray can be provided through a handpiece or it could be provided with another separate device. Finally, a connection to a computer and the control system 106 of the energy source 102 will allow the system 100 to utilize electronic or other thermal sensing means and obtain feedback control signals for the handpiece. An optimum cooling strategy might be one that uses a post-irradiation cooling spurt that provides cooling or dissipation of the epidermal heat generated by absorption of energy in the non-isotropic skin, optionally containing various pigmentation levels. An appropriate cryogen spray would be liquid nitrogen or tetrafluoroethane, $C_2H_2F_4$, an environmentally compatible, non-toxic, non-flammable freon substitute. In clinical application the distance between the aperture of the spray valve and the skin surface should be maintained at about 20 millimeters.

In a preferred embodiment of the present invention, upon delivery of laser energy onto the surface and therethrough, the target tissue will be raised to the optimal treatment temperature and generally not any higher, in an adequately rapid process, with the surface temperature of the skin remaining at a temperature below the threshold for damage temperature. It will be understood that the threshold for damage temperature is the temperature below which the skin or other tissue can be elevated without causing temporary or permanent thermal damage, and above which the tissue may undergo either transient or long term thermally induced physiological change. As described, the wavelength of irradiated light energy is selectively absorbed by hemoglobin or hair follicles, or other tissue with pigmentation or chromophores of a certain type, but passes through the surface and overlaying/adjacent tissue to the target tissue with minimal absorption. However, once the target tissue or structure becomes elevated in temperature, surrounding and adjacent tissue will become hot due to conduction of heat from the target tissue or structures. Post-irradiation cooling can then be initiated, and tissue other than the target tissue is prevented from increasing in temperature beyond the threshold of damage or adverse effect. Adverse effects of elevated tissue surface temperature include discomfort or pain, thermal denaturing of proteins and necrosis of individual cells at the surface only, or deeper tissue ablation potentially leading to hyperplasia, scarring, or hyperpigmentation, a proliferation of cells formed in response to the induced trauma. In a preferred embodiment of the method of the present invention, heating and subsequent post-cooling are performed in a predetermined timing sequence, optionally with the use of timer circuits and/or other controller means.

Thus, it will be obvious to those skilled in the art that a passive heat sink includes glass or sapphire tip probes, and other types of devices to lay on the surface of the skin. It will also be obvious that a dynamic type of heat sink will refer to those actively cooled by flowing gas or liquid, jets or spurts of coolant such as freon, and other active types of heat exchangers suitable for surface cooling while irradiating sub-surface portions of collagen tissue. U.S. Pat. No. 5,820,626 issued Oct. 13, 1998 to Baumgardner and U.S. application Ser. No. 08/938,923 filed Sep. 26, 1997 by Baumgardner et al., both incorporated herein by reference in their entireties, teach a cooling laser handpiece with refillable coolant reservoir, and can be utilized as a handpiece for delivery device 112 and heat sink 114.

Figure 2:
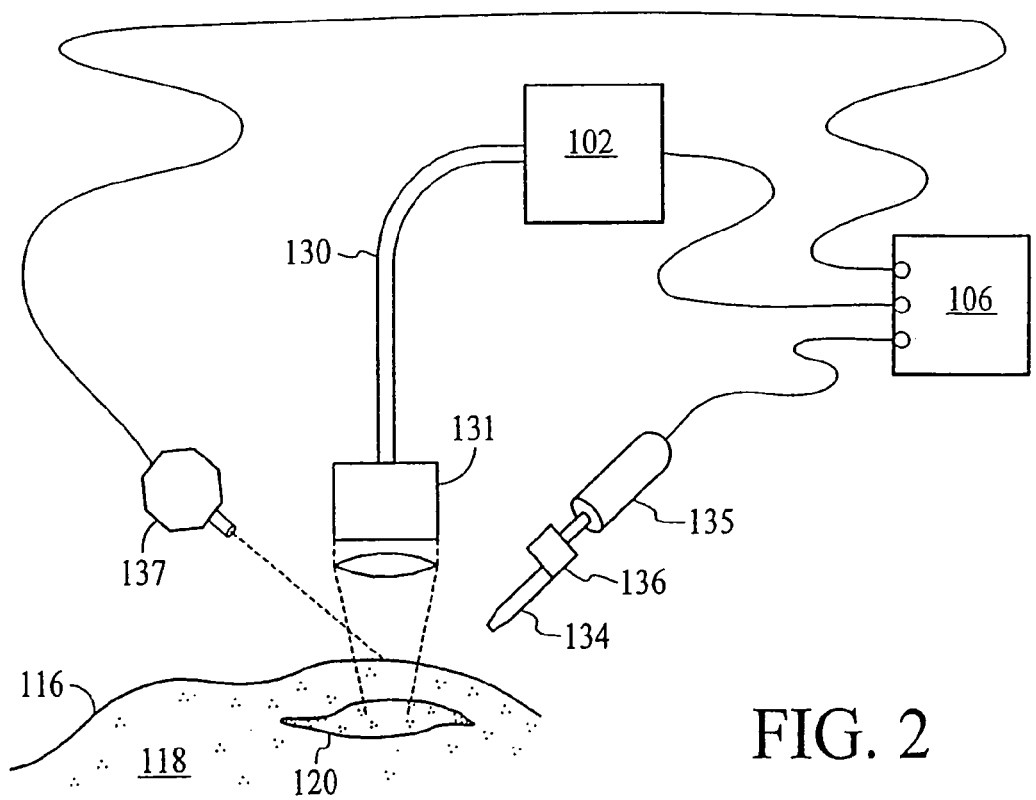
FIG. 2 is a more detailed representative schematic block diagram of a preferred embodiment of the delivery device shown in FIG. 1 of the present invention.

FIG. 2 is a more detailed representative schematic block diagram of a preferred embodiment of the delivery device 112 shown in FIG. 1 of the present invention. The energy from the energy source 102 is directed into delivery device 112 via a delivery channel 130 which may be a fiber optic, articulated arm, or an electrical cable etc. At the distal end of delivery device 112 is a energy directing means 131 for directing the pulsed energy toward the surface tissue 116 and overlaying tissue 118 overlaying the target tissue or structure 120. A nozzle 134 is useful for directing coolant from reservoir 135 to the tissue 118, and a valve 136 for controlling the coolant interval. A temperature sensor 137 may be used to monitor the temperature rise of the target tissue 118. Control system 106 monitors the temperature signal from sensor 137 and controls valve 136 and energy source 102. Reservoir 135 may be in the delivery device 112 or elsewhere, and contains a refrigerant which may be applied to surface tissue 120 by spraying said refrigerant from cooling nozzle 124 in conjunction with delivery of pulsed treatment energy to the patient.

Figure 3:
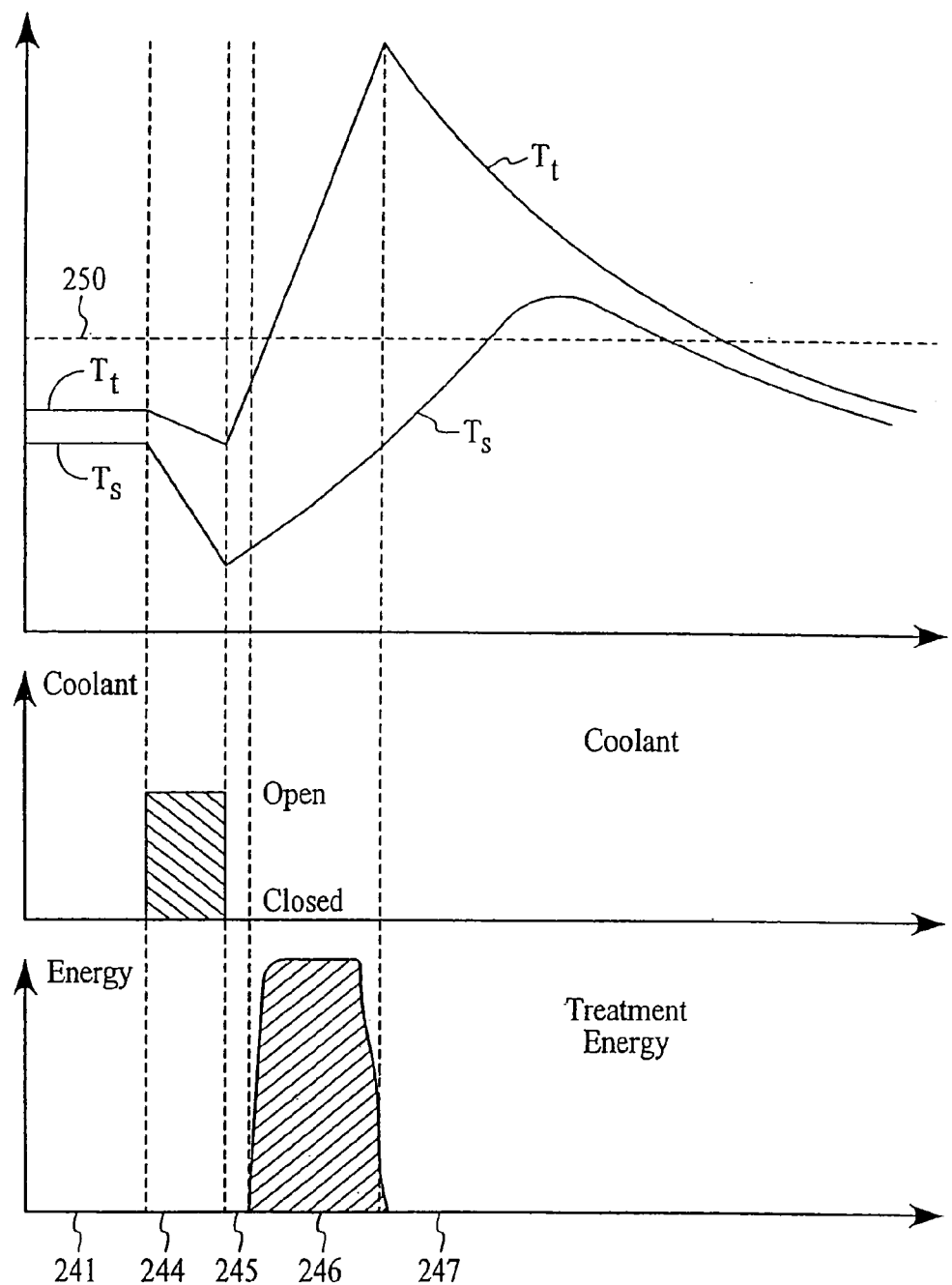
FIG. 3 is a representative sample data plot of the temperature of surface tissue and target tissue achieved by methods and systems of the prior art having precooling.

FIG. 3 is a representative sample data plot of the temperature of surface tissue 116 and target tissue 120 achieved by methods and systems of the prior art having precooling. The waveforms are representative of oscilloscope-type traces which reproduce signals generated by one or more thermal detectors. In general, with precooling the coolant is applied just prior to the delivery to the pulsed energy. Waveform 240 indicates the periods of time and associated temperatures of the target tissue and the surface tissue during the processes of the prior art. Initially, as indicated by time period 241, the temperature of the surface tissue 116 as well as the target tissue 120, as shown in FIGS. 1 and 2, are at $T_s$ and $T_t$ respectively. It will be understood that typically the skin surface is at a temperature somewhat below actual body temperature. Typically, this range might be between about 28 and about 34 degrees Celsius. Furthermore, a target vein, hair follicle or other structure can be assumed to be at about or somewhat just below 37 degrees Celsius, or actual body temperature. Once the refrigerant is applied to surface tissue 116 by opening valve 136 during a subsequent time period 244, the temperature $T_s$ drops to a level determined by the length of time 244 for which the surface tissue 120 is exposed to the coolant. By way of example, for time periods of about 30 milliseconds, $T_s$ may drop from a typical temperature of about 32 degrees Celsius to just above 0 degrees Celsius. However, as the target tissues 120 is deeper than the surface 116, initially $T_t$ is not significantly affected and may drop by only a few degrees. A short delay 245 following delivery of refrigerant may be used, and is typically between 0 and 100 milliseconds. This allows time for cooling of at least a layer of epidermis to a depth of 50 to 250 micrometers. Following time periods 244 and optional period 245, the pulsed energy is applied over predetermined or other time period 246. The time period 246 depends on the size of the target and the fluence delivered, as indicated by principles of selective photothermalysis. For example, in experiments with an Nd:YAG laser operating at 1064 nanometers, one application of a 10 millisecond period and a fluence of 50 joules per square centimeter was sufficient to treat small blood vessels, and fluences of up to 150 joules per square centimeter and time periods of up to 200 milliseconds are useful for treating larger vessels of 1 to 3 millimeters in cross-section. During period 246 $T_t$ increases to a therapeutically effective value, whereas $T_s$ remains below the threshold indicated as 250 for patient discomfort or tissue damage.

Subsequent to treatment, the target tissue 116 cools by conduction of thermal energy to adjacent overlaying tissue 118 including the surface tissue 116, with a resultant temperature rise in the target tissue 120 dependant on the size and depth of the target tissue 120. As $T_t$ equalizes with surrounding tissue, the T.sub.s may rise above the level of patient discomfort and even cause damage to surface tissue 116.

Figure 4:
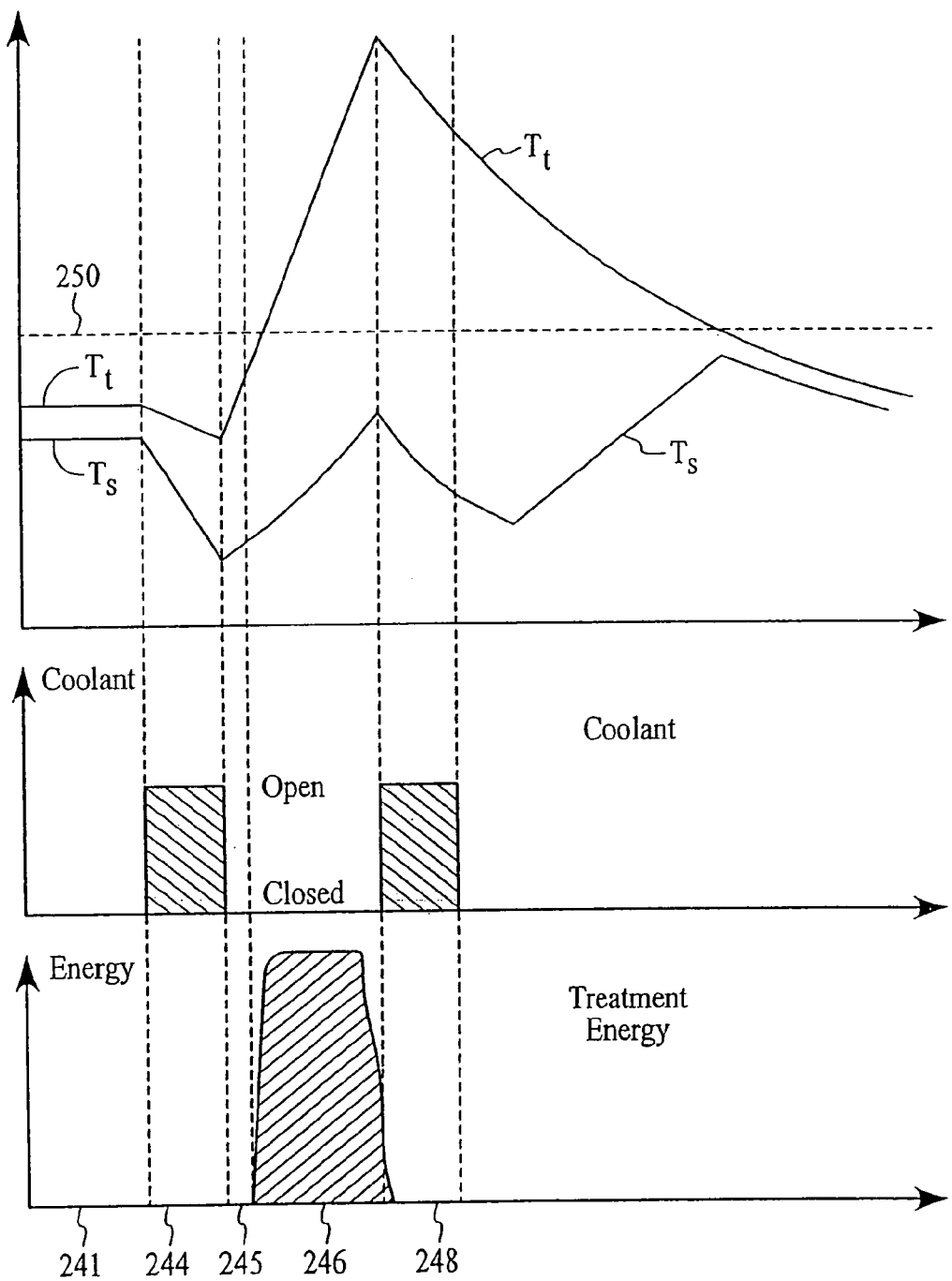
FIG. 4 is a representative sample data plot of the temperature of surface tissue and target tissue achieved by a preferred embodiment of the method and system of the present invention such as shown in FIGS. 1 and 2 having precooling.

FIG. 4 is a representative sample data plot of the temperature of surface tissue 116 and target tissue 120 achieved by a preferred embodiment of the method and system of the present invention such as shown in FIGS. 1 and 2 having precooling. The method of the present invention includes the process of precooling surface tissue 116 and target tissue 120 slightly, followed by a short time period 245 and subsequent delivery of thermal energy to the body during time period 246 such as shown in FIG. 3. In the present invention, however, refrigerant is also applied subsequent to the energy pulse by opening valve 136 as desired or as indicated, thus keeping T.sub.s below the threshold for damage temperature 250. FIG. 4 shows a pulse of coolant applied during time period 248 which is subsequent to the application of pulsed energy during period 246. This results in thermal quenching of the surface tissue 116. The thermal quenching pulse or other flow of refrigerant or other means for cooling is applied after the beginning of treatment period 246 and may be initiated before or after the end of time period 246. It is important that the peak or highest temperature of the surface tissue 116 never rise above the threshold for damage temperature 250. The time point at which the peak temperature in the surface tissue 116 is achieved is dependant on the size and depth of the target 120.

In one experimental example, cryogenic fluid was applied to the surface tissue 116 within 10 milliseconds of the end of the energy pulse of time period 246 and for a duration 248 of 20 milliseconds. For vascular treatment with an Nd:YAG laser with pulse widths of 5 milliseconds to 200 milliseconds, the period of thermal quenching 248 preferably 10 milliseconds to 30 milliseconds immediately after the treatment energy. This sequence significantly reduced patient discomfort compared to treatment with out thermal quenching. The effect of thermal quenching is not dependant on pre-cooling and may be used as the only method of cooling in many cases.

Figure 5:
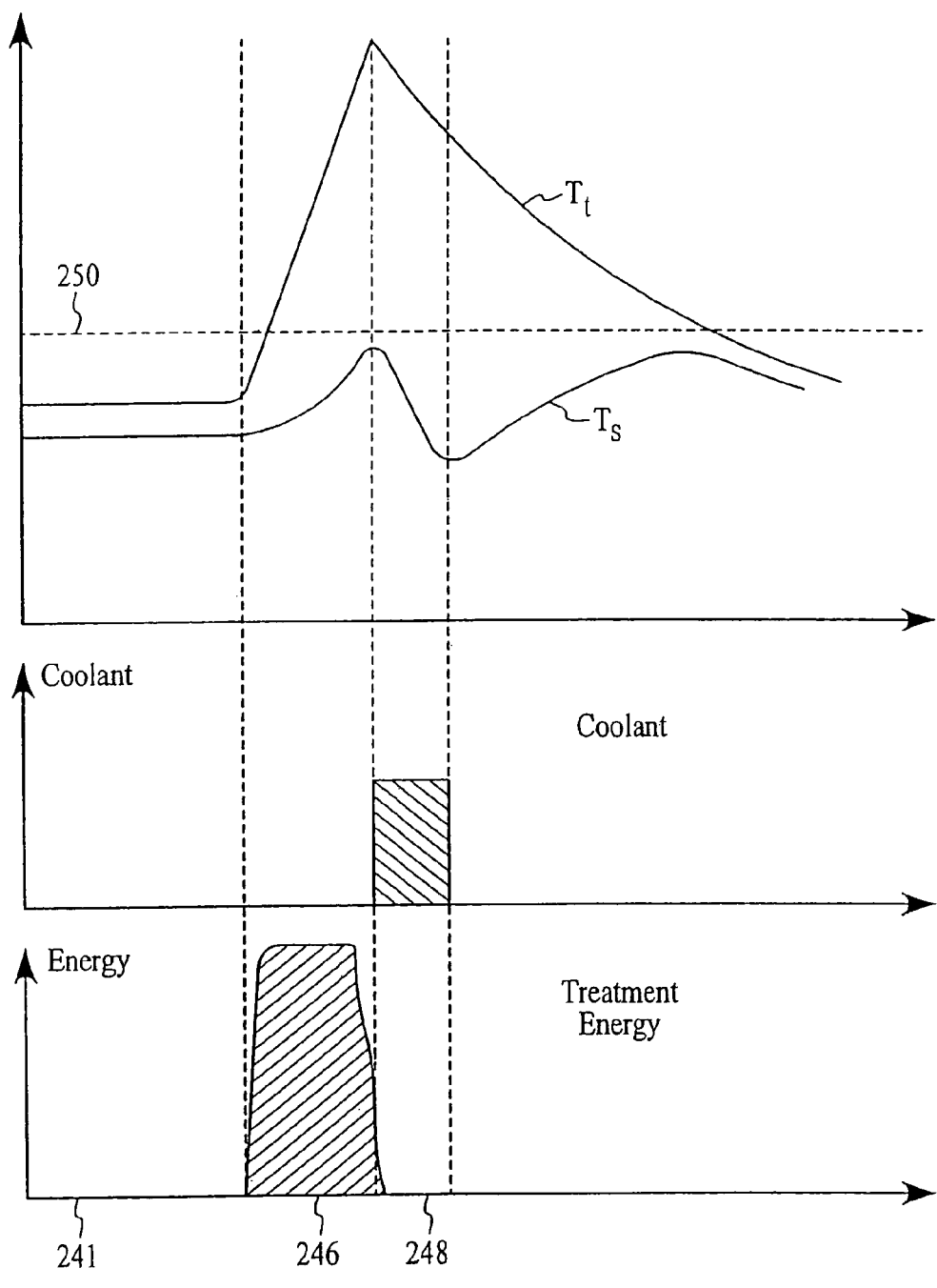
FIG. 5 is a representative sample data plot of the temperature of surface tissue and target tissue achieved by a preferred embodiment of the method and system of the present invention such as shown in FIGS. 1 and 2 without precooling.

FIG. 5 is a representative sample data plot of the temperature of surface tissue and target tissue achieved by a preferred embodiment of the method and system of the present invention such as shown in FIGS. 1 and 2 without precooling. As in the method shown in FIG. 4, the thermal quenching pulse or other flow of refrigerant or other means for cooling over time period 248 is applied after the beginning of treatment period 246 and may be initiated before or after the end of time period 246. It is important that the peak or highest temperature of the surface tissue 116 never rise above the threshold for damage temperature 250.

The present invention requires less cooling of the target tissue, structure or area during the treatment phase than is typically required, resulting in more efficient heating of the selected target and less thermal damage to surrounding tissue.

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function may have like reference numerals associated therewith.

In a preferred embodiment of the present invention, re-heating of tissue, especially target or subsurface tissue can be useful. U.S. application Ser. No. 09/185,490 filed Nov. 3, 1998 by Koop et al. entitled Subsurface Heating of Tissue teaches methods and systems for performing subsurface heating of material and tissue, and is incorporated herein by reference in its entirety. With these methods and apparatus, target or subsurface tissue is preheated to an elevated, non-destructive temperature which is somewhat below that of treatment. Thereafter, the temperature of the target tissue or structures is raised to treatment temperature. Once this second increase in temperature is achieved, the target tissue or structures will conduct heat into the body, especially to adjacent tissue and surface tissue, at which time the post-cooling of the present invention can be initiated so as to prevent damage to adjacent tissue or dermis or other surface tissue.

In one embodiment the invention utilizes an Nd:YAG laser at 1320 nm wavelength, (such as the CoolTouch 130, CoolTouch Corp., Auburn Calif.) as the source of treatment energy. At 1320 nm the absorption depth in tissue is such that energy is deposited throughout the upper dermis, with most absorption in the epidermis and upper dermis, a region including the top 200 to 400 microns of tissue. The energy falls off approximately exponentially with the highest level of absorbed energy in the epidermis. Optical heating of skin follows exposure to the laser energy. If the time of exposure to the laser is very short compared to the time required for heat to diffuse out of the area exposed, the thermal relaxation time, than the temperature rise at any depth in the exposed tissue will be proportional to the energy absorbed at that depth. However, if the pulse width is comparable or longer to the thermal relaxation time of the exposed tissue than profile of temperature rise will not be as steep. Conduction of thermal energy occurs at a rate proportional to the temperature gradient in the exposed tissue. Lengthening the exposure time will reduce the maximum temperature rise in exposed tissue.

For instance, at 1.3 microns the laser pulse width may be set to 30 milliseconds and fluence to less than 30 joules per square centimeter. This prevents excessive heat build up in the epidermis, which is approximately the top 100 microns in skin. The papillary dermis can then be heated to a therapeutic level without damage to the epidermis. The epidermis will reach a temperature higher than but close to that of the papillary dermis.

The epidermis is more resilient in handling extremes of temperature than most other tissue in the human body. It is therefore possible to treat the papillary dermis in conjunction with the epidermis without scarring or blistering, by treating both layers with laser energy and allowing a long enough exposure time such that the thermal gradient between the epidermis and underlying layers remains low. In this way the underlying layers can be treated without thermal damage to the epidermis.

It is known that thermal damage in tissue is time dependant and brief exposures to high temperature levels may be tolerated in situations where long exposures are lethal or injurious. Terminating the exposure of the epidermis to elevated temperatures will decrease the risk of damage to the epidermis. In this invention thermal quenching is used to terminate the exposure of the epidermis to elevated temperatures. In this embodiment cryogen spray cooling is use to reduce the epidermal temperature following the exposure to laser radiation. The laser heats the epidermis and lower layers simultaneously because of penetration of the laser energy into tissue. The cryogen cooling works from the top surface and heat flows out of the lower layers by conduction over a time period equivalent to the thermal relaxation time at each depth of tissue. As a result the epidermis is heated for a shorter time period than the papillary dermis or other deeper layers.

In this invention a top layer of tissue can be protected by limiting the time of exposure to elevated temperatures, and deeper layers are protected by the attenuation of light energy in tissue water.

The depth of protection due to cooling is determined by the degree of cooling and the time delay after laser exposure. In the embodiment described here 30 milliseconds of cooling spray is applied without delay, (within 5 milliseconds), after the termination of the laser exposure. The cooling may be delayed to cause longer thermal exposures of the surface. The amount of cooling is enough to reduce the temperature of the surface to non-therapeutic levels. Higher cooling levels will terminate heat build up deeper in tissue.

A wavelength of 1.3 microns is used in this embodiment to treat the middle layers of skin. Other wavelengths such as 1.45 or 2.1 microns may by used to treat more superficial layers of skin by this method. It is important that the wavelength is chosen such that there is absorption in tissue water such that the energy attenuation versus depth is fairly uniform over an area of skin. The range of wavelengths longer than 1100 nm in the infrared have this property. It is important that the energy source used for this invention is uniformly attenuated with depth in tissue. Ultrasound, microwaves, and RF electrical current are examples.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

In a preferred embodiment of the present invention, re-heating of tissue, especially target or subsurface tissue can be useful. U.S. application Ser. No. 09/185,490 filed Nov. 3, 1998 by Koop et al. teaches methods and systems for performing subsurface heating of material and in incorporated herein by reference in its entirety. In these methods, target or subsurface tissue is preheated to an elevated, non-destructive temperature which is somewhat below that of treatment. Thereafter, the temperature of the target tissue or structures is raised to treatment temperature. Once this second increase in temperature is achieved, the target tissue or structures will conduct heat into the body, especially to adjacent tissue and surface tissue, at which time the post-cooling of the present invention can be initiated so as to prevent damage to adjacent tissue or dermis or other surface tissue.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.P Thus, specific embodiments and applications of thermal quenching of tissue have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A method for treatment of acne scars in skin, comprising:
    heating the target skin portion with a source of energy which is uniformly attenuated with depth in skin for a predetermined time period and predetermined fluence such that the exposure time of the epidermis and the peak temperature reached by the epidermis are such that the epidermis does not blister;
    causing thermally mediated injury in skin below the epidermis; and
    causing resulting transient erythema to initiate a healing response which improves the appearance of the acne scars.

2. A method for treatment of photo damaged skin, comprising:
    heating the skin with a source of energy which is uniformly attenuated with depth in skin for a predetermined time period and predetermined fluence such that the exposure time of the epidermis and the peak temperature reached by the epidermis are such that the epidermis does not blister; and
    causing thermal mediated injury in skin below the epidermis; and
    causing transient erythema upon treatment, thereby initiating a healing response which improves the appearance of the photo damaged skin.

3. A method for treatment of wrinkled skin, comprising:
    heating the skin with a source of energy which is uniformly attenuated with depth in skin for a predetermined time period and predetermined fluence such that the exposure time of the epidermis and the peak temperature reached by the epidermis are such that the epidermis does not blister;

causing thermal mediated injury in skin below the epidermis; and causing transient erythema upon treatment, thereby initiating a healing response which improves the appearance of the wrinkled skin.

* * * * *